US009594078B2

(12) United States Patent
Choi et al.

(10) Patent No.: US 9,594,078 B2
(45) Date of Patent: Mar. 14, 2017

(54) CHROMATOGRAPHIC ASSAY SYSTEM

(75) Inventors: Young Ho Choi, Princeton, NJ (US); Jaean Jung, Monroe Township, NJ (US)

(73) Assignee: ACCESS BIO, INC., Somerset, NJ (US)

( * ) Notice: Subject to any disclaimer, the term of this patent is extended or adjusted under 35 U.S.C. 154(b) by 0 days.

(21) Appl. No.: 12/241,583

(22) Filed: Sep. 30, 2008

(65) Prior Publication Data

US 2010/0081214 A1 Apr. 1, 2010
US 2012/0003756 A9 Jan. 5, 2012

Related U.S. Application Data

(63) Continuation of application No. 10/838,584, filed on May 3, 2004, now abandoned.

(60) Provisional application No. 60/467,717, filed on May 2, 2003.

(51) Int. Cl.
| G01N 33/558 | (2006.01) |
| G01N 33/551 | (2006.01) |
| G01N 33/533 | (2006.01) |
| G01N 33/543 | (2006.01) |
| G01N 21/84 | (2006.01) |

(52) U.S. Cl.
CPC ..... *G01N 33/533* (2013.01); *G01N 33/54306* (2013.01); *G01N 33/54366* (2013.01); *G01N 33/558* (2013.01); *G01N 21/8483* (2013.01); *G01N 2458/40* (2013.01); *Y10T 436/143333* (2015.01)

(58) Field of Classification Search
USPC ... 422/56–61; 435/7.1, 7.2, 7.34, 7.93, 7.94, 435/7.96, 287.8, 287.9, 805, 969, 970; 436/514, 518, 528, 530, 541
See application file for complete search history.

(56) References Cited

U.S. PATENT DOCUMENTS

| 4,444,879 | A | * | 4/1984 | Foster et al. ............... 435/7.95 |
| 5,859,215 | A |   | 1/1999 | Rodriguez-Ubis et al. |
| 6,001,658 | A |   | 12/1999 | Fredrickson |
| 6,194,221 | B1 | * | 2/2001 | Rehg et al. ................ 436/514 |
| 6,341,182 | B1 | * | 1/2002 | Fitzgerald .......... G01N 15/1475 |
|   |   |   |   | 382/205 |
| 7,285,424 | B2 | * | 10/2007 | Song .................. G01N 21/274 |
|   |   |   |   | 435/239 |
| 2002/0187563 | A1 | * | 12/2002 | Hofstraat ................ 436/518 |

FOREIGN PATENT DOCUMENTS

| JP | 2003-83970 | 3/2003 |
| WO | WO 94/01775 | 1/1994 |
| WO | WO 99/30131 | * 6/1999 |

OTHER PUBLICATIONS

Harma et al., "Europium Nanoparticles and Time-resolved Fluorescence for Ultrasensitive Detection fo Prostate-Specific Antigen". Clinical Chemistry. 47:3. 2001. 561-568.*

* cited by examiner

*Primary Examiner* — Chris L Chin
(74) *Attorney, Agent, or Firm* — Lucas & Mercanti, LLP

(57) ABSTRACT

The present application discloses an analyte detection apparatus having at least one reservoir area and a wicking membrane, wherein a labeled specific binding partner is impregnated on the reservoir area; and a region on the wicking membrane where at least one chemical component is immobilized.

10 Claims, 11 Drawing Sheets

CHROMATOGRAPHIC ASSAY SYSTEM

CROSS REFERENCE TO RELATED APPLICATIONS

The present application is a continuation application of U.S. patent application Ser. No. 10/838,584, filed May 3, 2004 now abandoned, which claims the benefit of priority to U.S. Provisional Patent Application No. 60/467,717, filed on May 2, 2003.

BACKGROUND OF THE INVENTION

1. Field of the Invention

The invention relates to the field of high sensitivity detection of molecules, especially biomolecules. The invention also relates to using fluorescent labels.

2. General Background and State of the Art

Ultrasensitive immunoassay methods are developed and used in clinical diagnostics to measure extremely low concentrations of specific compounds in highly complex samples. Although the sensitivity, reliability, rapidity, simplicity, and cost of these methods have steadily improved, further improvements are still needed and possible (Hampl J, et al., Upconverting phosphor reporters in chromatographic assays. *Analytical Biochemistry,* 2001; 288, 176-187; Unger M. et al, Single-molecule fluorescence observed with mercury lamp illumination. *Biotechniques* 1999; 27:1008-1014; and Weiss S. Fluorescence spectroscopy of single biomolecules. *Science* 1999; 283:1676-1683). The current trend toward miniaturized, multianalyte methods has introduced its own challenges and requirements for immunoassay technology (Taylor J R, et al., Probing specific sequences of single DNA molecules with bioconjugated fluorescent nanoparticles. *Anal Chem* 2000; 72:1979-1986; and Zijlmans, et al., Detection of cell and tissue surface antigens using up-converting phosphors: a new reporter technology. *Anal Biochem* 1999; 267:30-36). The interest in new label technologies has especially increased because none of the commonly used direct or enzyme-amplified radioactive, colorimetric, luminescent, or fluorescent reporters fulfills all of the requirements for an ideal label, including specific activity, size, nontoxicity, cost, stability, localization, and detection. Directly detectable labels such as fluorophores suffer from limited sensitivity, and enzyme-amplified or dissociation-enhanced methods lose spatial information.

Recently, new detection methods based on high specific-activity particulate labels, such as quantum dots, luminescent inorganic crystals, up-converting phosphors, fluorescent nanoparticles, and plasmon resonant particles, have been introduced to respond to future demands for clinical diagnostics and biological, genomic, and pharmaceutical research. These submicrometer-sized labels are coupled to specific binding reagents such as nucleic acid probes, receptors, lectins, enzymes, and antibodies to detect specific molecules with sensitivities equal to or better than the best conventional labels available. In spite of the large molecular size and obvious stearic problems, these particular labels have also been used successfully in solid-phase immunoassays. It has been recognized, however, that the production, colloidal stability, and nonspecific binding of particle-protein bioconjugates may still require further improvements.

Time-resolved fluorometry and lanthanide labels were introduced for immunoassays 20 years ago. Since then, the dissociation-enhanced lanthanide fluoroimmunoassay (DELFIA®) technology has been known as one of the most sensitive and reliable immunoassay platforms. The research on intrinsically fluorescent, inert, and stable lanthanide chelate and cryptate labels has led to the development of novel homogeneous and heterogeneous assays that are expected to be introduced into routine clinical diagnostics. Moreover, an advanced dissociation-enhanced technology, based on lanthanide cofluorescence, which amplifies the long-lifetime fluorescence of europium(III), terbium(III), samarium(III), and dysprosium(III), has been known. A unique feature of lanthanide chelate fluorescence, the absence of self-quenching effects from multiple labeling, makes them ideal and suitable for high-density cluster labels such as dyed latex nanoparticles. The highly fluorescent chelates used in the DELFIA technology can also be used in fluorescent lanthanide(III) chelate nanoparticle because the hydrophobic environment inside the latex protects the fluorescent chelates from environmental effects, such as solvent quenching, and stabilizes the kinetically weak complexes. The adaptation of appropriate chelates for all four lanthanides would enable a nanoparticle-based, quadruple-labeling technology with an extremely low detection limit and a direct, surface readout measurement.

Detecting low levels of target marker in a sample using classic fluorochrome is sometimes difficult and prone to errors because specific fluorescence signals tend to be low and are usually mixed with nonspecific signals. Furthermore, autofluorescence produced from specimen can cause interference. The fluorescence half-life of complex chelate of lanthanide elements—e.g., europium (EU)—is as much as six orders of magnitude longer than conventional fluorescent labels. Consequently, the emission from lanthanide chelate can be distinguished from background fluorescence (which has a short decay half-life) by using a time-resolved fluorometer with an appropriate delay, counting, and cycle times. This unique dye confers luminescence with a decay time of >500 µs, far longer than that of conventional fluorescent probes or autofluorescent samples, typically having decay times of <50 µs. Thus, time-resolved fluorometry can virtually eliminate autofluorescence.

These europium luminescent dyes feature long-wavelength emissions (~610 nm) that are well separated from the excitation peak (~365 nm). This unusually large Stokes shift permits the use of filter combinations that effectively isolate the desired luminescence signal (Harma et al., Europium nanoparticles and time-resolved fluorescence of ultrasensitive detection of prostate-specific antigen. 2001; 47:561-568). In the DELFIA system, lanthanide ions are dissociated from the chelating structure into the fluorescence enhancement solution. This additional enhancing step is required to provide an environment that effectively eliminates quenching water and contains energy-absorbing chelating compounds to transfer energy further to lanthanide ions. The lanthanide phosphors can be detected directly without any enhancing steps due to the water-protecting crystal structure. The disadvantage of using the lanthanide phosphors is the lack of light-absorbing groups that effectively transfer the absorbed energy to the lanthanide ions. Frank and Sundberg realized, in the late 1970s, that by combining these properties into a latex particle, fluorescent particles with a very high specific activity could be prepared. They prepared latex particles which contained a thenoyltrifluoroacetone lanthanide chelate complexed with tri-n-octylphosphine oxide (naphtoyltrifluoroacetone in the DELFIA technology complexed with tri-n-octylphosphine oxide) providing particles without quenching effects but having a light-absorbing group inside the particle. The polymer shell efficiently removes fluorescence-quenching water from the vicinity of the chelate by producing a hydrophobic environment. Extremely sensitive assays can be carried out using such particle labels (Härmä et al., 2001, Soukka et al., 2001a). These nanosized polymer labels contain 30,000-2,000,000 europium molecules entrapped by β-diketones, which have one of the highest quantum yields of the known lanthanide chelators (Harma et al., Europium nanoparticles and time-resolved fluorescence of ultrasensitive detection of prostate-specific antigen. 2001; 47:561-568). This encapsulation has no negative effect on the fluorescence efficiency. For a 100 nm size europium particle, the fluorescence yield is equivalent to about 3,000 molecules of fluorescein. Phycobiliprotein B-PE (perhaps the most fluorescent substance known) has a fluorescence yield equivalent to about 30 fluorescein molecules. Since a 100 nm particle is about 10 times the diameter of phycobiliprotein B-PE and a thousand times greater in volume/mass, these europium particles are 100 times more fluorescent than B-PE on a molar basis. This particle will give ultrasensitivity for assay because of its great fluorescence, broad stoke shift and long-lived luminescence. Encapsulation: 30,000-2,000,000 europium molecules in a single particle.

SUMMARY OF THE INVENTION

The present invention is directed to a highly sensitive assay system, including but not limited to time-resolved fluorescent dye used in a lateral flow assay format, which ensures improved sensitivity while maintaining the beneficial aspects of lateral flow assay.

In one respect, the present invention is directed to a chromatographic test system that uses highly sensitive europium particle as a label. Chromatographic assay can give rapid result, conveniently (mostly one step) with reasonable sensitivity. In another aspect, the invention is directed to a sensitive nucleic acid detection device and system thereof. Application of a fluorescent rare earth chelate incorporated into a matrix provides a highly sensitive assay.

In another aspect, the invention is directed to a genetic materials detection system for the presence of analytes such as RNA virus, DNA virus, RNA or DNA of the cell components via either a non-polymerase chain reaction or polymerase chain reaction nucleic acid-based approach. This detection system is fast, easy to use and has high sensitivity and specificity.

The advantages of the invention include the following:

This system is extremely sensitive, which is an essential requirement for analytes detection.

The inventive product can be used on-site, reducing the need for sample transportation to off-site premises.

The immediate alert of positive results within about 15 min more or less after sample preparation is possible with the inventive product. It is to be understood that while one of the advantages of the inventive system is that rapidity of the detection system, the invention is not limited to any particular time of obtaining results. The results may be obtained in the ballpark of 20 minutes, 30 minutes 40 minutes or somewhat longer, depending on various conditions.

Assay procedure for this one-step method is simple to perform and test result is reading within 15 minutes more or less and does not require any additional steps.

The inventive product can be performed by personnel without advanced education and professional skills.

The inventive product can be stored at room temperature whereas other commercial products generally require refrigeration.

In another aspect of the invention, the invention is directed to a Point-of-Care Testing or various settings of testing for the various analytes because it is 1) Simple step, 2) Field-usable, 3) Utilizes stable reagents, 4) No special storage, and 5) Rapid results.

The present invention is directed to an analyte detection apparatus having at least one reservoir area and a wicking membrane, wherein a labeled specific binding partner is impregnated on the reservoir area; and a region on the wicking membrane where at least one chemical component is immobilized. As used in the apparatus, the label may be a rare earth chelate, in particular a lanthanide(III) chelate, and further in particular, the label may be europium(III), terbium(III), samarium(III), or dysprosium(III), or a combination thereof.

In the apparatus, the analyte may be without limitation an antigen, an antibody, a nucleic acid or a hapten. The specific binding partner may be without limitation an antigen, an antibody, a nucleic acid, biotin or biotin analogue, streptavidin, avidin or a hapten. And the chemical component may be an antigen, an antibody, a nucleic acid, biotin or biotin analogue, streptavidin, avidin or a hapten.

In one aspect of the invention, the apparatus may be a lateral flow assay format apparatus.

In another aspect of the invention, the invention is directed to a method of determining the presence of at least one type of an analyte in a sample comprising applying an amount of the sample to the apparatus described above, wherein if at least one type of analyte is present in the sample, the sample migrates to the wicking membrane where a chemical reaction occurs, wherein presence of a signal indicates that the analyte is present in the sample. In the practice of this invention, the signal may be generated by a rare earth chelate, in particular a lanthanide(III) chelate, and further in particular, the label may be europium(III), terbium(III), samarium(III), or dysprosium(III), or a combination thereof.

In this method, the sample may be a biological sample. Further, the sample may be without limitation blood, serum, plasma, urine, saliva, sweat and liquid media processed from a biological or environmental sample. The analyte detected may be an antigen, an antibody, a nucleic acid or a hapten. And the chemical reaction may be with an antigen, an antibody, a nucleic acid, biotin or biotin analogue, streptavidin, avidin or a hapten. A plurality of analytes in a sample may be detected. The apparatus used in the method may be without limitation a lateral flow assay format apparatus. And the analyte may be specific to a pathogen.

The present invention is also directed to a kit comprising a compartment that contains the apparatus described above, and instructions for using the apparatus as described above.

The present invention is also directed to high sensitivity nucleic acid detection system. The nucleic acid based detection system of the invention is able to amplify a signal from a low concentration of specific genomic DNA or RNA sequences from biological samples. This method is also unique, specific, simple, and the amplifying system is easy to operate in a field-deployable detection module.

Time-resolved fluorometry technology is a system based on europium embedded micro particles conjugated with oligonucleotides, peptide nucleic acid (PNA), antigens or antibodies.

Any disease markers or environmental substances that require highly sensitive tools for their detection may make use of this technology.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein.

DETAILED DESCRIPTION OF THE INVENTION

Figure 1:
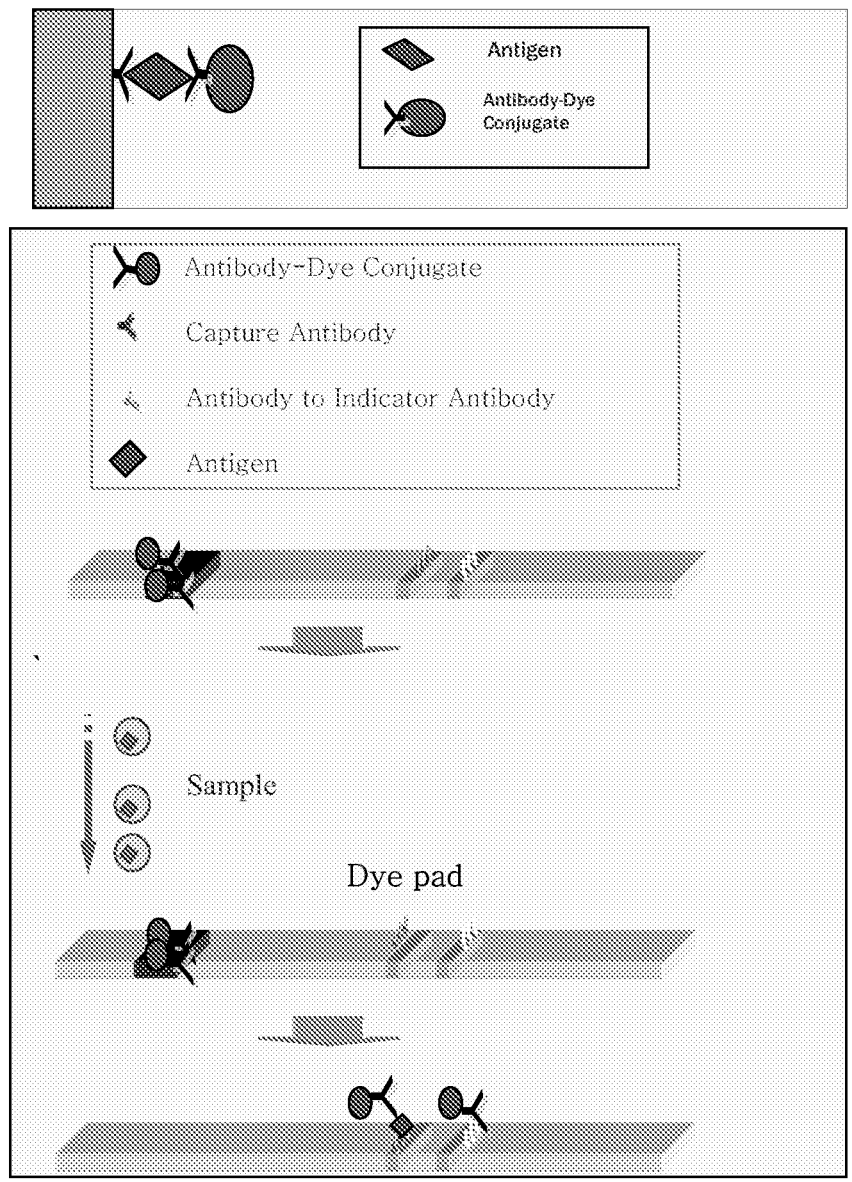
FIG. 1 shows a schematic depiction of the inventive device.

In the present application, "a" and "an" are used to refer to both single and a plurality of objects.

As used herein, "base member" refers to a solid material, which provides support and unity for the strip. This support may be constructed from a thin sheet of glass, paper or plastic which has been cut to a size appropriate to include entire assay contents while providing convenience to the user.

As used herein, "dry porous carrier" or "wicking membrane" refers to a substance that is porous enough to allow migration of liquid and contiguous to filter element. Typical materials for use in a dry porous carrier include, but are not limited to, nylon, cellulose, polysulfone, polyvinylidene difluoride, cellulose acetate, polyurethane, fiberglass, and nitrocellulose.

As used herein, "filter" may be fashioned from any number of filter materials. Typical filter materials for use may include, but are not limited to, cellulose, polyesters, polyurethanes, nylon and fiberglass. Such a filter area may include a reservoir pad and absorbent pad.

As used herein, "fluorescent rare earth chelate" may be described in U.S. Pat. Nos. 4,259,313 and 4,283,382, which patents are incorporated herein by reference in their entirety. Thus, this invention describes method of utilizing long-lived fluorescent compositions prepared by incorporating chelates of the rare earth metals, preferably europium and terbium, into polymeric matrix such as latex particles. The chelating agent strongly absorbs light and efficiently transfers energy to the metal. The latex configuration confers aqueous stability to fluorescent rare earth chelates, which in the past have been subject to quenching in aqueous liquids. The polymeric beads derived from the latex and having the rare earth chelate incorporated therein can then be used as fluorescent labels to form labeled reagents by adsorbing or covalently binding antigens, antibodies, plant lectins, carbohydrates or other such proteinaceous compounds, lipids and nucleic acids to the surface of the polymeric latex beads.

As used herein, "impregnated" refers to reagents which are incorporated in the assay system, wherein they are either dried or lyophilized onto or into the assay system.

As used herein, "polymeric particle" refers to a spherical or near-spherical polymer particle at various sizes. Preferably, the size is about 0.05-0.5 µm in diameter. However, it is understood that the invention is not limited to the use of any particular type of polymeric particle. In its broadest sense, any substance or particle that can encapsulate the fluorescent dye is encompassed by the present invention.

As used herein, "specific binding reagent" or "specific binder" or "specific binding partner" includes, but is not limited to, antibody, antigen, hapten, hapten-macromolecule (e.g. bovine serum albumin) conjugate, avidin, streptavidin, biotin, biotin-macromolecule (e.g. bovine serum albumin) conjugate, oligonucleotide, peptide nucleic acid and nucleic acid genetic material.

As used herein, "tag" refers to a substance that is labeled to the specific binding reagent, which is labeled with time-resolved fluorescent dye. The tag reacts specifically to specific binder immobilized on solid phase. In particular, the tag may be biotin when the specific binder immobilized on solid phase is avidin or streptavidin. The tag may be a hapten when the specific binder immobilized on solid phase is antibody that is specific to the hapten of the tag.

As used herein, "time-resolved fluorometer" refers to a tool for measuring time dependence of fluorescence intensity after a short excitation pulse which can also be made as a function of emission wavelength.

Chromatographic Amplification

In one aspect, the present invention is directed to a apparatus that is suitable for rapid chromatographic tests.

The inventive test may be performed on-site by a lay person with minimal training while rapid results are obtained after adding one or two drops of sample to a disposable test device or card or strip. The results may be read visually without any further intervention. In one aspect of the invention, the procedure for the proposed test may be as follows. For discussion purposes only, the test may be discussed in terms of an antigen/antibody reaction. However, it is to be understood that the assay is not limited an antigen/antibody complex. For any molecule of interest for which a specific binding partner is known, the specific binder may be used and impregnated into the apparatus to assay for the presence of the molecule of interest. Such molecule of interest and its specific binding partner may include without limitation, antigen/antibody, ligand/receptor, nucleic acid/nucleic acid, nucleic acid/antibody, lipid/specific binding partner such as an antibody, carbohydrate/specific binding partner such as an antibody and so on. For purposes of illustration only, in the following discussions, antigen/antibody and nucleic acid/nucleic acid interactions are primarily discussed, with the understanding that the principles of using specific binding partners is applicable to any type of molecule from any sample source.

A liquid sample is added to the test device or card or strip. As the fluid wicks/moves across the card the target antigens react with labeled specific antibodies embedded in the dye pad. The material flows into a membrane where a set of unlabeled antibodies are immobilized in at least one distinct zone(s). The antigen-labeled antibody complex is retained/captured creating (a) defined line(S) for reading. This line can be detected by a reader equipped with time-resolved fluorescence or any other suitable detection mechanism. In a separate control zone, the excess-labeled antibody in the test reacts with embedded non-specific antibody to provide assurance that the key test component is functioning properly, thereby being useful as a positive control. A non-limiting principle of the test is further seen in FIG. 1.

A liquid sample is added to the test device or card or strip. As the fluid wicks/moves across the card the target antigens react with labeled specific antibodies embedded in the dye pad. The material flows into a membrane where a set of unlabeled antibodies are immobilized in at least one distinct zone(s). The antigen-labeled antibody complex is retained/captured creating (a) defined line(S) for reading. This line can be detected by a reader equipped with time-resolved fluorescence or any other suitable detection mechanism.

Chromatographic assay in the form of a lateral flow assay, for instance, is an amplification system. The target antigens in a liquid sample are steadily concentrated by the high-affinity antibodies immobilized on a membrane when they are moving through the membrane by capillary power. As a result, even though the antigen may be at a very low concentration in the actual sample, the concentration of the antigen captured at the test line or test zone is much higher than in the sample. Also, capillary migration supplies target antigens continuously to the immobilized antibody.

Usually, when the capture antibody forms a complex with an antigen as in a conventional assay, there is a decrease of micro-environmental antigen concentration surrounding the capture antibody immobilized on the solid phase. In general, this depletion of antigen around the antibody immobilized on the solid phase is one of the major problems in assay sensitivity, especially with microplate assays and chip-based assay, since this causes an actual decrease of antigen concentration around the antibody.

In an alternative embodiment, the three-dimensional structure of a bibulous membrane (e.g. nitrocellulose) provides more surface area for antibody binding to solid phase. This allows the chromatographic assay to have significantly more capturing capacity than other two dimensional assay systems (e.g. microplate assay).

Figure 2:
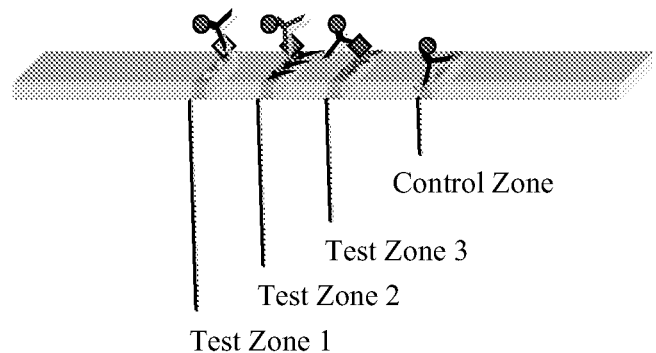
FIG. 2 shows the inventive device for detecting a plurality of analytes.

The invention is also directed to multiple analyte detection system, which is conducted with only a single sampling and no further procedural steps with the inventive chromatographic assay. If various antibody-dye conjugates are embedded in the dye pad area and antibody specific for each antigen is respectively immobilized in a separate zone on the membrane, each test line provides distinctive information for each specific antigen for the specific agent (FIG. 2). It is also contemplated that the device may detect more than one type of analyte. For instance, by way of example, referring to FIG. 2, Test zone 1 may be impregnated with an antibody to detect an antigen; Test zone 2 may be impregnated with a receptor to detect a ligand; and Test 3 may be impregnated with a nucleic acid for sequence specific binding.

In one aspect, the invention is directed to a signal amplification system using fluorescent europium particles that contain about 30,000-1,000,000 europium atoms in a single particle. This system may be an improved chromatographic assay with advantageous features such as 1) Simple testing procedure, 2) Field-usable, 3) Utilizes stable reagents, 4) No special storage required, and 5) Rapid results. The amplified signal can be detected by a small, portable reader that provides quantitative or qualitative results.

Figure 3:
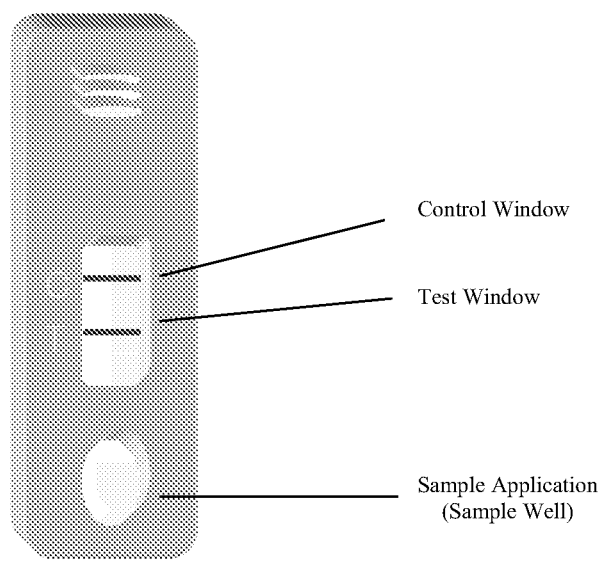
FIG. 3 shows picture of a test device.
Figure 4:
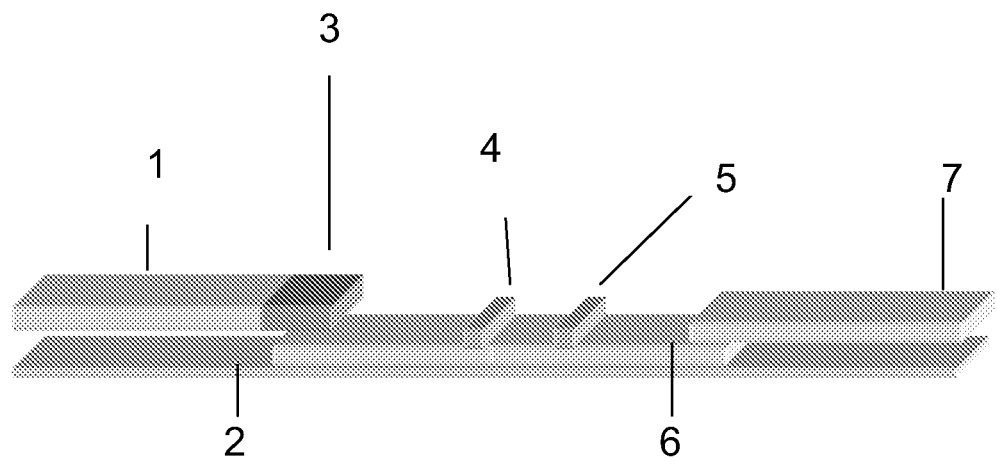
FIG. 4 shows a configuration of rapid chromatographic detection system.
Figure 5:
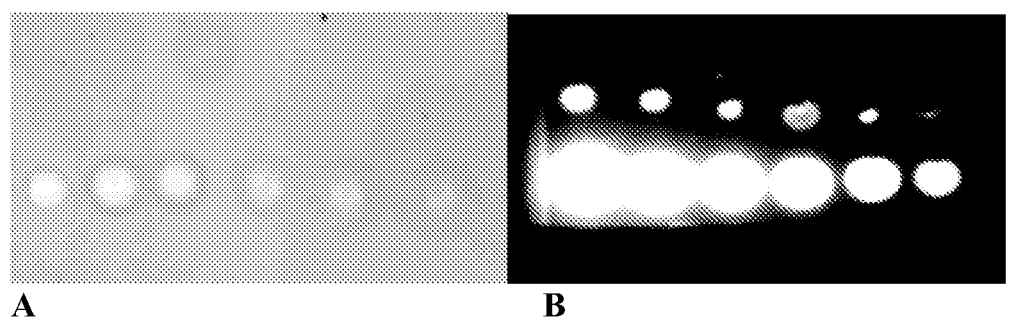
FIGS. 5A and 5B show (A) Image result of colloidal gold antibody conjugate, (B) Image result of europium particle.
Figure 6:
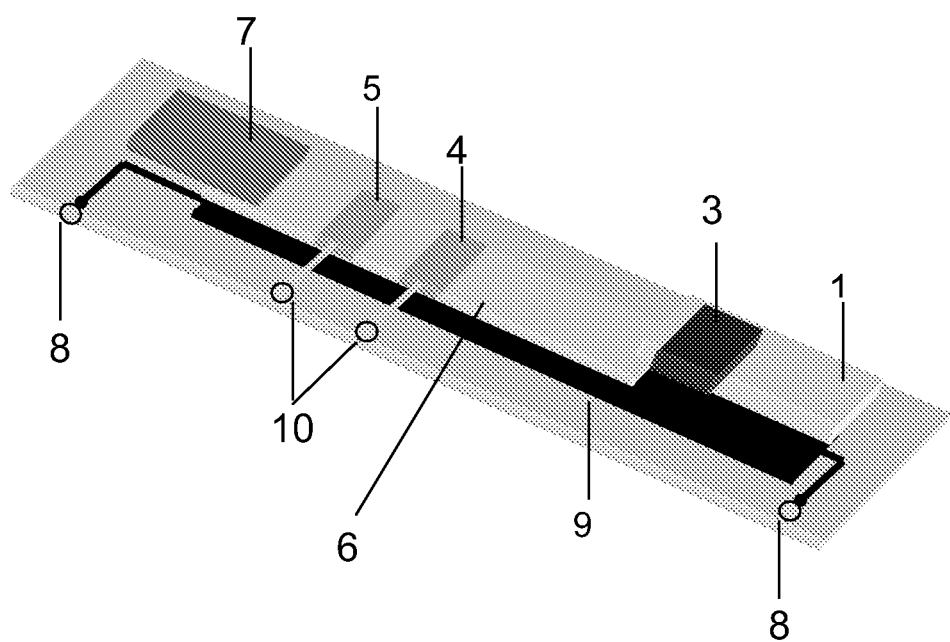
FIG. 6 shows a configuration of rapid nucleic acid detection system.
Figure 7:
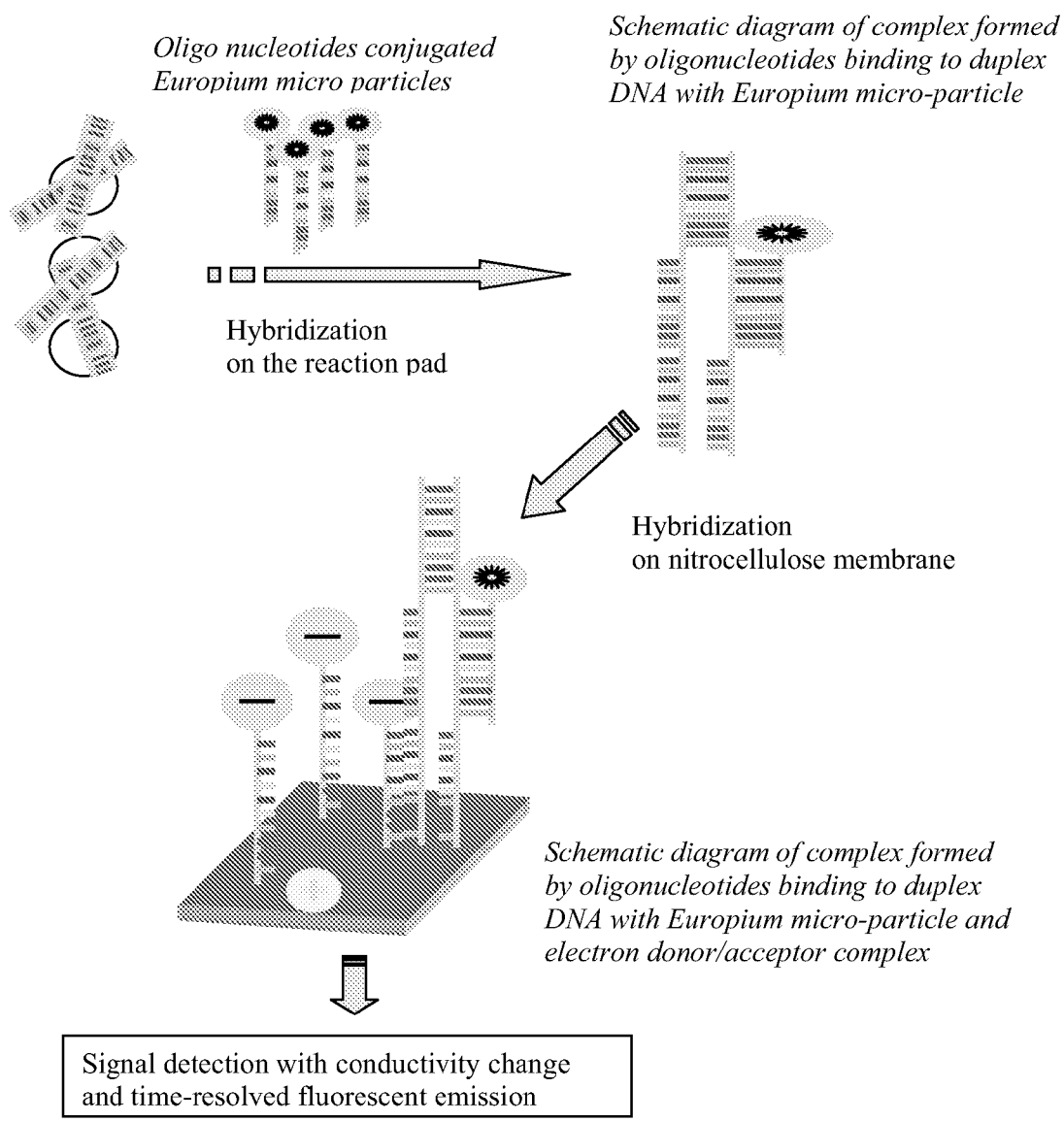
FIG. 7 shows a diagram of assay principle for detection of a specific DNA sequence in a sample, such as from a biological pathogen.
Figure 8:
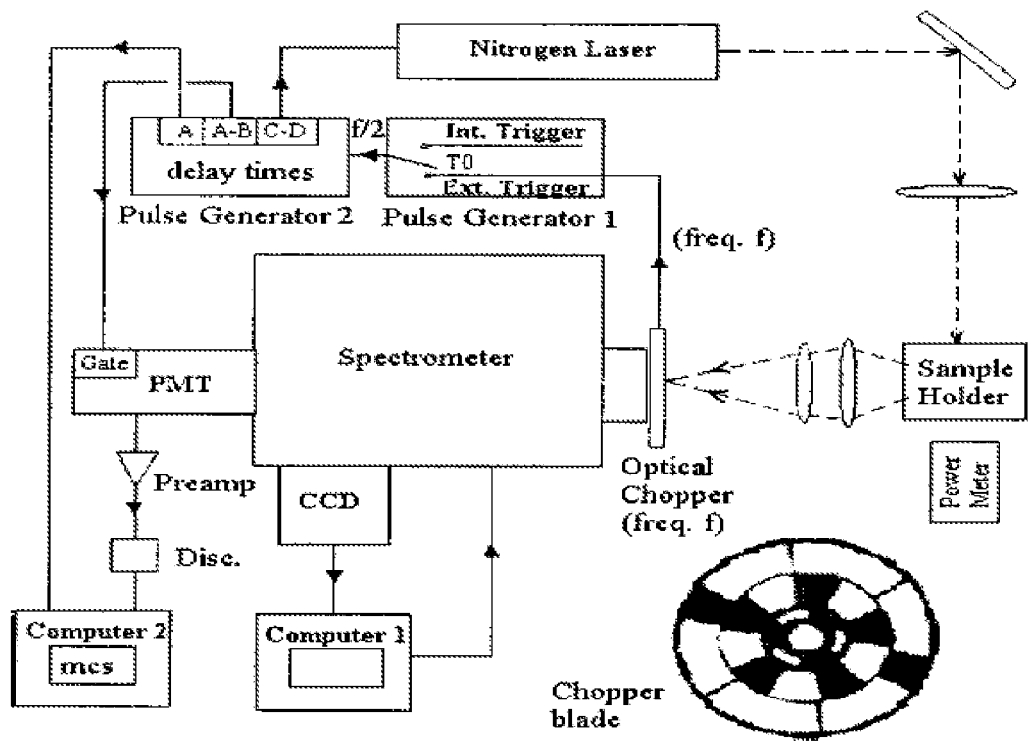
FIG. 8 shows an instrument for measuring time-resolved lanthanide emission (Xiao, M and Selvin, P R. An improved instrument for measuring time-resolved lanthanide emission and resonance energy transfer. *Review of scientific instruments* 1999; 70(10):3877-81).
Figure 9:
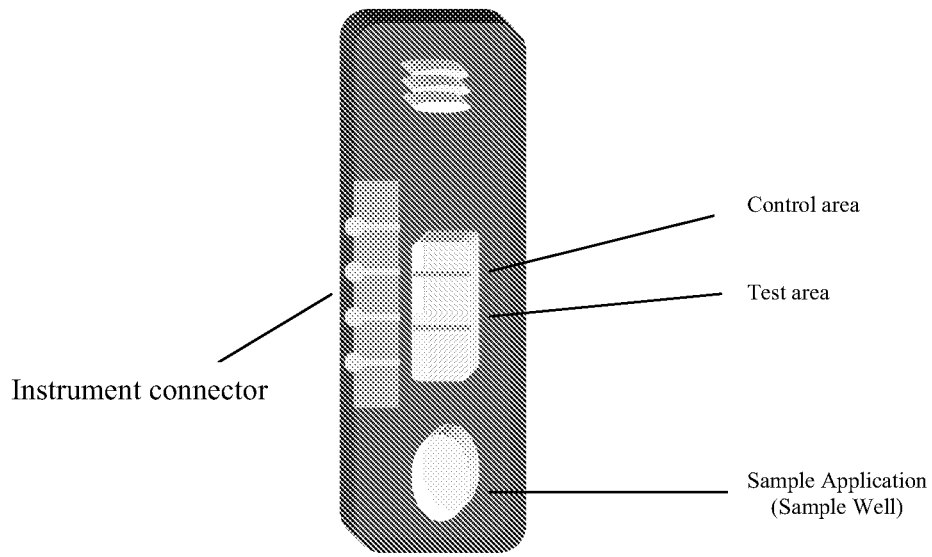
FIG. 9 shows picture of a test device.

The test strip may be enclosed within a case, which is preferably a disposable plastic case, but may be made with any substance, which is able to contain the contents safely. The test kit may contain a plurality of windows, preferably at least two windows or openings, at least one to view the control and/or test lines or test bands, and the other providing a well to receive the sample (FIG. 3). Referring to FIG. 4, inside the device may be a test strip with preferably two pads. The first pad, the reservoir area 1 or sample well may be used for the uptake of the sample and the removal of interfering materials from sample. In addition, the first pad may contain europium particle-specific binding partner conjugates 3 in a specially formulated buffer system. The labeled specific binding reagent impregnated into the reservoir area may bind an analyte in the sample and the analyte/specific binding partner complex is wicked through a wicking membrane 6 until a test band 4 is formed, where another specific binder of the analyte captures the analyte/specific binding partner complex thus forming a test band. The sample is further wicked and encounters a binding partner to the specific binding partner impregnated in the wicking membrane, and a control band 5 is established. The second pad 7, absorbent pad, may be used for removing excess fluid that has already passed through the reaction membrane. The first pad, second pad and wicking membrane are connected to a plastic plate 2.

Two types of reagents may be separately immobilized on the membrane as thin lines or bands. The antibody that is specific to the conjugate antibody may be immobilized in the control window, while the antibody that is specific to an analyte such as a biothreat agent or any agent that is desired to be detected is immobilized in the test window (FIGS. 3 and 4).

Chromatographic Assay Principle

The inventive test kit is designed to be a self-performing device. It may contain all of the reagents and components in precise quantities to generate test results after sample addition, as shown in FIG. 1. The sample passes first through the reservoir pad that contains various materials. It may contain (a) buffer(s) to optimize the pH of the sample, (a) detergent(s) to suspend all components in the sample, and (a) porous filter(s) to generate proper flow through the device. The sample subsequently flows, by capillary action or diffusion, to the dye area or dye pad, where the test agents react with the labeled specific binder, which is preferably labeled with an europium particle-label, which is specific to the agent. The reaction complex then migrates through the wicking membrane where the non-reacted binding sites of the agent react with immobilized specific binder, and generating a line or band in the test window. The depleted sample and remainder of the unbound dye complex continue to migrate to the control window where antibody specific to the conjugate antibody is immobilized to retain the dye complex and form a control line. It is also contemplated that the reaction complex may encounter the control region before reaching the test region.

In one aspect of the invention, the result is a solid-phase chromatographic assay for the qualitative or quantitative detection of a bio agent. In the test procedure, about 60 μL of liquid sample may be added to the sample application area and the result may be provided by the instrument within about 15 minutes more or less. It is to be understood that while the rapidity of the assay is an advantageous feature of the inventive system, the exact time to obtain the result may vary depending conditions and sample. Accordingly, the present invention is not limited by any particular time of assay.

Embodiment 1

Figure 10:
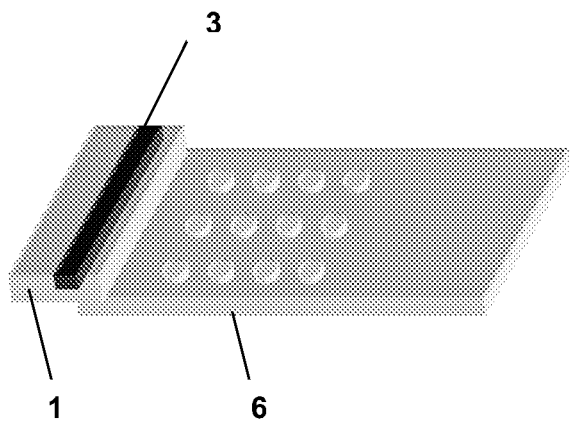
FIG. 10 shows an embodiment of the test strip.

In one embodiment of the detection apparatus, the apparatus includes the following features:
At least one filter element 1 having impregnated one or more specific binding reagent(s) labeled with fluorescent label comprising a fluorescent rare earth chelate incorporated into a polymeric particle 3; and
A dry porous carrier 6 (e.g. nitrocellulose membrane) which is porous enough to allow migration of liquid and contiguous to filter element, wherein
At least one specific binding reagent is immobilized in at least one zone of the dry porous carrier (FIG. 10).

Embodiment 2

Figure 11:
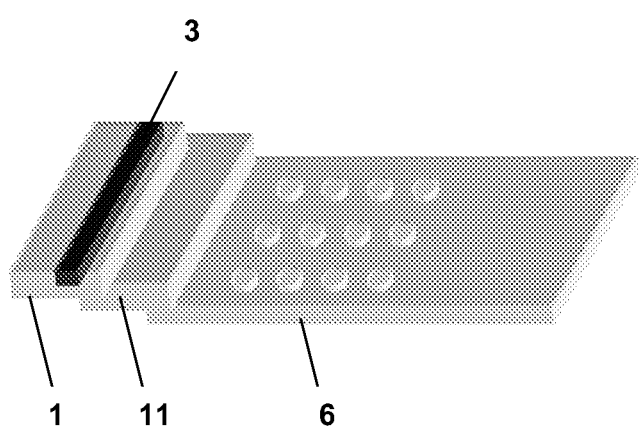
FIG. 11 shows an embodiment of the test strip.

In another embodiment of the detection apparatus, the apparatus includes the following features:
At least one first filter element 1 having impregnated one or more specific binding reagent(s) labeled with fluorescent label comprising a fluorescent rare earth chelate incorporated into a polymeric particle 3;
At least one second filter element 11 which is interposed between the first filter element and dry porous carrier and which is porous enough to allow migration of liquid; and
A dry porous carrier 6 (e.g. nitrocellulose membrane) which is porous enough to allow migration of liquid and contiguous to the second filter element, wherein
At least one specific binding reagent is immobilized in at least one zone of the dry porous carrier (FIG. 11).

Embodiment 3

Figure 12:
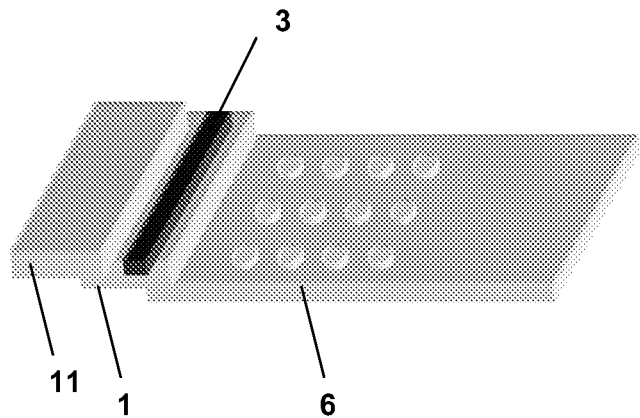
FIG. 12 shows an embodiment of the test strip.

In another embodiment of the detection apparatus, the apparatus includes the following features:
At least one first filter element 1 which is interposed between the second filter element 11 and dry porous carrier 6, and which is porous enough to allow migration of liquid, and which has impregnated one or more specific binding reagent(s) labeled with fluorescent label comprising a fluorescent rare earth chelate incorporated into a polymeric particle 3;
At least one second filter element 11 which is contiguous to the first filter element 1 and which is porous enough to allow migration of liquid; and
A dry porous carrier 6 (e.g. nitrocellulose membrane) which is porous enough to allow migration of liquid and contiguous to the first filter element, wherein
At least one specific binding reagent is immobilized in at least one zone of the dry porous carrier (FIG. 12).

Embodiment 4

Figure 13:
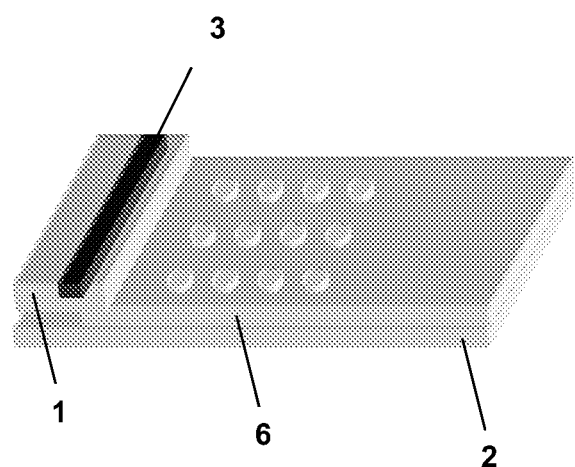
FIG. 13 shows an embodiment of the test strip.

In another embodiment of the detection apparatus, the apparatus includes the following features:
A base member 2;
An array disposed on base member 2, array comprising:
At least one filter element 1 having impregnated one or more specific binding reagent(s) labeled with fluorescent label comprising a fluorescent rare earth chelate incorporated into a polymeric particle 3; and
A dry porous carrier 6 (e.g. nitrocellulose membrane) which is porous enough to allow migration of liquid and contiguous to filter element, wherein
At least one specific binding reagent is immobilized in at least one zone of the dry porous carrier (FIG. 13).

Embodiment 5

Figure 14:
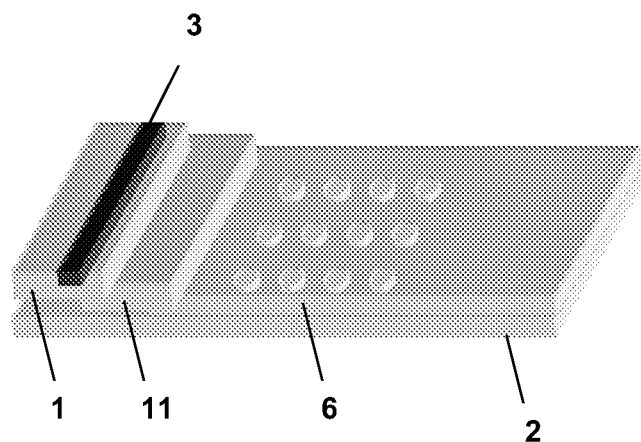
FIG. 14 shows an embodiment of the test strip.

In another embodiment of the detection apparatus, the apparatus includes the following features:
A base member 2;
An array disposed on base member 2, array comprising:
At least one first filter element 1 having impregnated one or more specific binding reagent(s) labeled with fluorescent label comprising a fluorescent rare earth chelate incorporated into a polymeric particle 3;
At least one second filter element 11 which is interposed between the first filter element 1 and dry porous carrier 6 and which is porous enough to allow migration of liquid; and
A dry porous carrier 6 (e.g. nitrocellulose membrane) which is porous enough to allow migration of liquid and contiguous to the second filter element, wherein
At least one specific binding reagent is immobilized in at least one zone of the dry porous carrier (FIG. 14).

Embodiment 6

Figure 15:
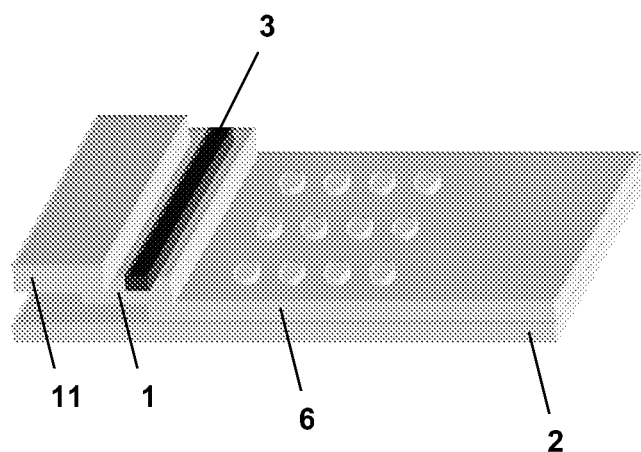
FIG. 15 shows an embodiment of the test strip.

In another embodiment of the detection apparatus, the apparatus includes the following features:
A base member 2;
An array disposed on base member 2, array comprising:
At least one first filter element 1 which is interposed between the second filter element 11, and which is porous enough to allow migration of liquid, and which has impregnated one or more specific binding reagent(s) labeled with fluorescent label comprising a fluorescent rare earth chelate incorporated into a polymeric particle 3;
At least one second filter element 11 which is contiguous to the first filter element 1 and which is porous enough to allow migration of liquid; and
A dry porous carrier 6 (e.g. nitrocellulose membrane) which is porous enough to allow migration of liquid and contiguous to the first filter element 1, wherein
At least one specific binding reagent is immobilized in at least one zone of the dry porous carrier (FIG. 15).

Embodiment 7

Figure 16:
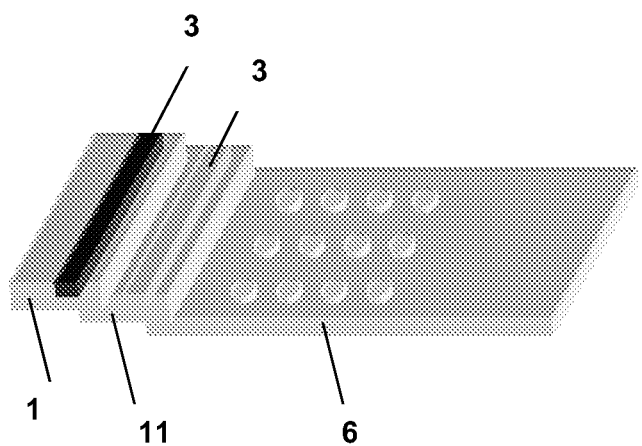
FIG. 16 shows an embodiment of the test strip.

In another embodiment of the detection apparatus, the apparatus includes the following features:
At least one first filter element 1 having impregnated one or more specific binding reagent(s) labeled with fluorescent label comprising a fluorescent rare earth chelate incorporated into a polymeric particle 3;
At least one second filter element 11 which has impregnated one or more specific binding reagent(s) labeled with tag that is specifically reactive to the specific binding reagent immobilized in dry porous carrier 6, and which is interposed between the first filter element 1 and dry porous carrier 6 and which is porous enough to allow migration of liquid; and A dry porous carrier 6 (e.g. nitrocellulose membrane) which is porous enough to allow migration of liquid and contiguous to the second filter element, wherein At least one specific binding reagent is immobilized in at least one zone of the dry porous carrier (FIG. 16).

Embodiment 8

Figure 17:
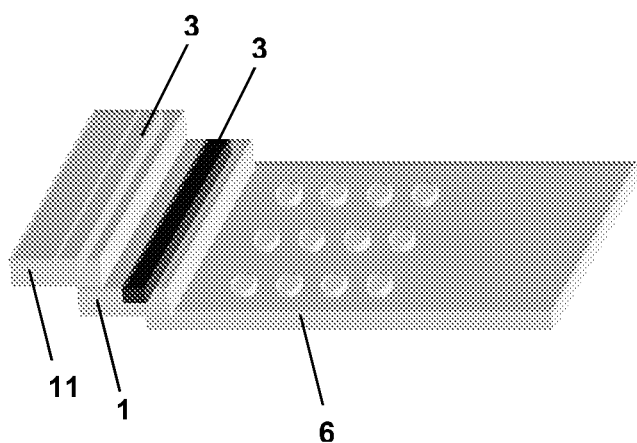
FIG. 17 shows an embodiment of the test strip.

In another embodiment of the detection apparatus, the apparatus includes the following features:

At least one first filter element 1 which is interposed between the second filter element 11, and which is porous enough to allow migration of liquid, and which has impregnated one or more specific binding reagent(s) labeled with fluorescent label comprising a fluorescent rare earth chelate incorporated into a polymeric particle 3;

At least one second filter element 11 which has impregnated one or more specific binding reagent(s) labeled with tag 3 that is specifically reactive to the specific binding reagent immobilized in dry porous carrier 6, and which is contiguous to the first filter element 1 and which is porous enough to allow migration of liquid; and A dry porous carrier 6 (e.g. nitrocellulose membrane) which is porous enough to allow migration of liquid and contiguous to the first filter element 1, wherein At least one specific binding reagent is immobilized in at least one zone of the dry porous carrier (FIG. 17).

Embodiment 9

Figure 18:
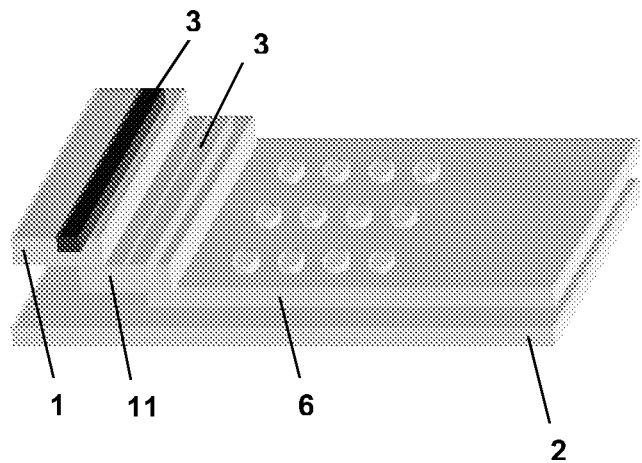
FIG. 18 shows an embodiment of the test strip.

In another embodiment of the detection apparatus, the apparatus includes the following features:

A base member 2;

An array disposed on base member, array comprising:

At least one first filter element 1 having impregnated one or more specific binding reagent(s) labeled with fluorescent label comprising a fluorescent rare earth chelate incorporated into a polymeric particle 3;

At least one second filter element 11 which has impregnated one or more specific binding reagent(s) labeled with tag that is specifically reactive to the specific binding reagent immobilized in dry porous carrier 6, and which is interposed between the first filter element 1 and dry porous carrier 6 and which is porous enough to allow migration of liquid; and A dry porous carrier 6 (e.g. nitrocellulose membrane) which is porous enough to allow migration of liquid and contiguous to the second filter element, wherein At least one specific binding reagent is immobilized in at least one zone of the dry porous carrier (FIG. 18).

Embodiment 10

Figure 19:
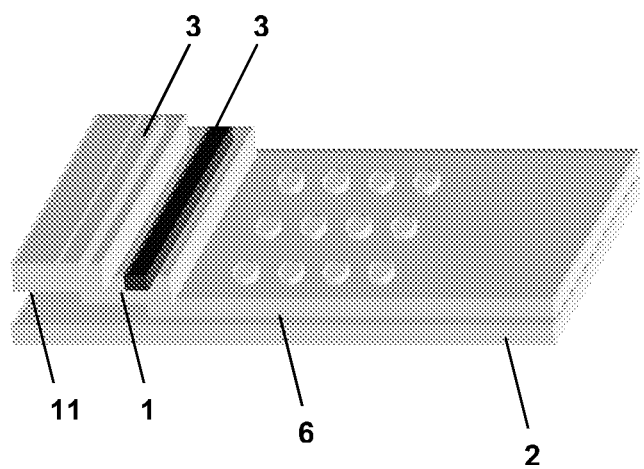
FIG. 19 shows an embodiment of the test strip.

In another embodiment of the detection apparatus, the apparatus includes the following features:

A base member 2;

An array disposed on base member 2, array comprising:

At least one first filter element 1 which is interposed between the second filter element 11, and which is porous enough to allow migration of liquid, and which has impregnated one or more specific binding reagent(s) labeled with fluorescent label comprising a fluorescent rare earth chelate incorporated into a polymeric particle 3;

At least one second filter element 11 which has impregnated one or more specific binding reagent(s) labeled with tag that is specifically reactive to the specific binding reagent immobilized in dry porous carrier 6, and which is contiguous to the first filter element 1 and which is porous enough to allow migration of liquid; and A dry porous carrier 6 (e.g. nitrocellulose membrane) which is porous enough to allow migration of liquid and contiguous to the first filter element 1, wherein At least one specific binding reagent is immobilized in at least one zone of the dry porous carrier (FIG. 19).

Sandwich Assays

Antibody-Antibody Sandwich

Specific binder immobilized on solid phase: monoclonal antibody and/or polyclonal antibody. Specific binding reagent labeled with fluorescent dye: monoclonal antibody and/or polyclonal antibody labeled with fluorescent dye.

Antibody-Antigen Sandwich

Antibody-Antigen Sandwich 1

Specific binder immobilized on solid phase: antigen specific to analyte antibody in sample (e.g. HIV-1 gp41 antigen that is specifically reactive to human anti-HIV-1 gp41 antibody)

Specific binding reagent labeled with fluorescent dye: secondary monoclonal antibody and/or polyclonal antibody labeled with fluorescent dye. This antibody is specific to the primary antibodies in samples.

Antibody-Antigen Sandwich 2

Specific binder immobilized on solid phase: secondary monoclonal antibody and/or polyclonal antibody. This antibody is specific to the primary antibodies in samples.

Specific binding reagent labeled with fluorescent dye: antigen (labeled with fluorescent dye) specific to analyte antibody in sample (e.g. HIV-1 gp41 antigen that is specifically reactive to human anti-HIV-1 gp41 antibody)

Antigen-Antigen Sandwich

Specific binder immobilized on solid phase: antigen specific to analyte antibody in sample (e.g. HIV-1 gp41 antigen that is specifically reactive to human anti-HIV-1 gp41 antibody)

Specific binding reagent labeled with fluorescent dye: antigen (labeled with fluorescent dye) specific to analyte antibody in sample (e.g. HIV-1 gp41 antigen that is specifically reactive to human anti-HIV-1 gp41 antibody)

This format comprising:

Specific binder (e.g. avidin or streptavidin) immobilized on solid phase; specific binding reagent labeled with tag(s) (e.g. biotin), which reacts specifically to specific binder immobilized on solid phase; specific binding reagent labeled with fluorescent dye.

This format is applicable to all assay formats described above with; replacing the specific binder immobilized on solid phase to the specific binder (e.g. avidin or streptavidin) immobilized on solid phase and the specific binding reagent labeled with tag.

Competition Assay

Format 1

Specific binding reagent (e.g. antibody specific to hapten) labeled with fluorescent dye: capable of binding to analyte of interest in sample to form reaction complex.

Specific binder (e.g. hapten) immobilized on solid phase: capable of reacting with free specific binding reagent labeled with fluorescent dye and capable of competitively displacing analyte from the reaction complex and reacting with specific binding reagent labeled with fluorescent dye.

Format 2

Specific binding reagent (e.g. antibody specific to hapten) immobilized on solid phase: capable of competitively binding to analyte of interest in sample or specific binder (e.g. hapten) labeled with fluorescent dye.

Specific binder (e.g. hapten) labeled with fluorescent dye: capable of competing with analyte of interest in sample.

Format 3

This format comprising:

Specific binder (e.g. avidin or streptavidin) immobilized on solid phase; specific binding reagent labeled with tag(s) (e.g. biotin), which reacts specifically to specific binder immobilized on solid phase; specific binding reagent (hapten) labeled with fluorescent dye.

This format is applicable to all assay formats described above with; replacing the specific binder immobilized on solid phase to the specific binder (e.g. avidin or streptavidin) immobilized on solid phase and the specific binding reagent labeled with tag.

Detection of Multiple Analytes

Another embodiment of the present invention permits the detection of multiple analytes in a single fluid sample by the presence of more than one specific type of labeled reagent and the same number of types of corresponding immobilized reagent. The device can be set up unidirectionally with multiple labeled reagents impregnated throughout the filter elements and multiple immobilized corresponding substances defined in several assay indicia zones on the dry porous carrier. In the bidirectional or multidirectional embodiment, more than one set of components such as the filter elements and dry porous carrier are associated with a common reservoir.

Kit and Instructions for Using the Kit

The present invention includes a kit for using the inventive detection apparatus. The kit may comprise a container made of cardboard, plastic or any other solid object or plastic bag, which may house the detection apparatus. Included in the kit may be instructions on how to use the kit. Such instructions may be written on the container or in written form placed inside the container such as a paper instruction sheet. Instructions for using the kit and the detection apparatus may also be in electronic format, on a website, in addition or in lieu of paper format. Instructions may also be placed in a catalog for selling the kit.

EXAMPLES

Example 1

Preparation of Troponin I Test Strip Using Europium Chelate Nanoparticle

Preparation of Anti-Troponin I Coated Nanoparticle

The carboxyl group of europium chelate nanoparticles were activated with 10 mmol/L N-(3-dimethylaminopropyl)-N'-ethylcarbodiimide and 100 mmol/L N-hydroxysulfosuccinimide for 30 min. The activated particle washed once with 50 mM MES buffer, pH 6.1. 20 mM/L anti-troponin I antibody was added. After 2 hour incubation, the antibody coated particles were washed three times with 50 mM MES buffer, pH 6.1.

Preparation of Dye Pad

The glass fiber filter was prepared by impregnating with a solution containing anti-troponin I antibody coated nanoparticle, 0.2% tween-20, 0.25% bovine serum albumin, 0.5% sucrose, 10 mM sodium phosphate, pH 7.5 to rectangular piece of glass fiber filter measuring 8 mm×305 mm and dried under constant vacuum in a lyophilizer. The pad was stored dry in a desiccator until use.

Preparation of Filter Pad

The glass fiber filter was treated with a solution of 0.05% Tween-20, 2% of sucrose, 1% of BSA and 100 mM sodium phosphate, pH 7.4, and then air dried at room temperature.

Immobilization of Antibody on Membrane

A double sided transparent tape (305 mm×25 mm size) was attached to 20 mm from the bottom of the thin plastic plate (305×60 mm). A nitrocellulose membrane was cut to 305 mm×25 mm size and attached directly on the top of the double sided tape. An assay indicia zone of immobilized test line for Troponin I was defined on the 9 mm from the bottom of the membrane by spraying 30 micro liter of solution of 1 mg/ml goat anti-troponin I antibody in 10 mM PBS, pH 7.5. For control band, 1 mg/ml of polyclonal anti-mouse IgG antibody was defined on the 13 mm from the bottom of the membrane by spraying. After spraying, the membrane was dried at ambient temperature for approximately 12 hours. The base and wicking membrane was stored in a desiccator until further processed.

Strip Construction

Dye pad was attached to plastic base right below the bottom of nitrocellulose membrane and the filter pad is attached adjacent to the dye pad. The plastic plate then was cut into a plurality of strips 60 mm in length and 4 mm in width so that each contains a linear array of nitrocellulose membrane, dye pad and filter pad.

Assay Method and Result:

When 70 micro liter sample was added into filter pad, a detectable signal began to appear in the assay indicia zone after incubation when the strip was exposed to UV light.

Example 2

Preparation of Troponin I Test Strip Using Colloidal Gold

Preparation of Gold Sol 1400 ml of deionized water was brought to a boil. Hydroauric acid (299 to 305 mg) was added, and boiling continued for 5 minutes. Sodium citrate (440 mg) dissolved in 10 ml of distilled water was poured into the gold solution and the solution boiled for another 10 minutes. The solution was allowed to cool to ambient room temperature.

Preparation of Label pH of gold sol was adjusted to 6.8 with 40 mM potassium carbonate. Same monoclonal antibody used in Example 1 was added to 50 ml of gold solution which was stirred vigorously for 30 min at ambient temperature. 1 ml of 15% bovine serum albumin was added, and the solution was continuously stirred for approximately 15 min at ambient temperature. Colloidal gold-monoclonal antibody conjugate was recovered by centrifugation at 10,000 rpm in GSA rotor for 1 hr, discarding the supernatant and suspending the resultant pellet in 25 ml of 2% bovine serum albumin in 10 mM sodium phosphate, pH 7.5. The suspension was then spun down at 10,000 rpm for 1 hr in GSA rotor. The supernatant once again was discarded and the pellet suspended in 6 ml of 2% bovine serum albumin in 10 mM sodium phosphate, pH 7.5.

Preparation of Dye Pad

The glass fiber filter was prepared by impregnating with a solution containing anti-troponin I antibody coated colloidal gold, 0.2% tween-20, 0.25% bovine serum albumin, 0.5% sucrose, 10 mM sodium phosphate, pH 7.5 to rectangular piece of glass fiber filter measuring 8 mm×305 mm and dried under constant vacuum in a lyophilizer. The pad was stored dry in a desiccator until use.

Preparation of Filter Pad

The glass fiber filter was treated with a solution of 0.05% Tween-20, 2% of sucrose, 1% of BSA and 100 mM sodium phosphate, pH 7.4, and then air dried at room temperature.

Immobilization of Antibody on Membrane

A double sided transparent tape (305 mm×25 mm size) was attached to 20 mm from the bottom of the thin plastic plate (305×60 mm). A nitrocellulose membrane was cut to 305 mm×25 mm size and attached directly on the top of the double sided tape. An assay indicia zone of immobilized test line for Troponin I was defined on the 9 mm from the bottom of the membrane by spraying 30 micro liter of solution of 1 mg/ml goat anti-troponin I antibody in 10 mM PBS, pH 7.5. For control band, 1 mg/ml of polyclonal anti-mouse IgG antibody was defined on the 13 mm from the bottom of the membrane by spraying. After spraying, the membrane was dried at ambient temperature for approximately 12 hours. The base and wicking membrane were stored in a desiccator until further processed.

Strip Construction

Dye pad was attached to plastic base right below the bottom of nitrocellulose membrane and the filter pad was attached adjacent to the dye pad. The plastic plate then was cut into a plurality of strips 60 mm in length and 4 mm in width so that each contains a linear array of nitrocellulose membrane, dye pad and filter pad.

Assay Method and Result:

When 70 micro liter sample was added into filter pad, a detectable signal began to appear in the assay indicia zone after incubation.

Example 3

Comparison of the Sensitivity of the Strips Prepared Using Each Method

The strip prepared in Example 1 and the strip prepared in Example 2 were tested to compare the sensitivity. The strip prepared in Example 1 showed 0.025 nanogram/ml of sensitivity while the strip prepared in Example 2 showed 0.5 nanogram/ml of sensitivity. The strip prepared using europium nanoparticle showed about 20 times more sensitive result than the strip prepared using colloidal gold.

Example 4

Preparation of hCG Test Strip Using Europium Nanoparticle

Preparation of Anti-hCG Coated Nanoparticle

The carboxyl group of europium chelate nanoparticles were activated with 10 mmol/L N-(3-dimethylaminopropyl)-N'-ethylcarbodiimide and 100 mmol/L N-hydroxysulfosuccinimide for 30 min. The activated particle washed once with 50 mM MES buffer, pH 6.1. 20 mM/L anti-hCG antibody was added. After 2 hour incubation, the antibody coated particles were washed three times with 50 mM MES buffer, pH 6.1.

Preparation of Dye Pad

The glass fiber filter was prepared by impregnating with a solution containing anti-hCG antibody coated nanoparticle, 0.2% tween-20, 0.25% bovine serum albumin, 0.5% sucrose, 10 mM sodium phosphate, pH 7.5 to rectangular piece of glass fiber filter measuring 8 mm×305 mm and dried under constant vacuum in a lyophilizer. The pad was stored dry in a desiccator until use.

Preparation of Filter Pad

The glass fiber filter was treated with a solution of 0.05% Tween-20, 2% of sucrose, 1% of BSA and 100 mM sodium phosphate, pH 7.4, and then air dried at room temperature.

Immobilization of Antibody on Membrane

A double sided transparent tape (305 mm×25 mm size) was attached to 20 mm from the bottom of the thin plastic plate (305×60 mm). A nitrocellulose membrane was cut to 305 mm×25 mm size and attached directly on the top of the double sided tape. An assay indicia zone of immobilized test line for hCG was defined on the 9 mm from the bottom of the membrane by spraying 30 micro liter of solution of 1 mg/ml monoclonal anti-hCG antibody in 10 mM PBS, pH 7.5. For control band, 1 mg/ml of polyclonal anti-mouse IgG antibody was defined on the 13 mm from the bottom of the membrane by spraying. After spraying, the membrane was dried at ambient temperature for approximately 12 hours. The base and wicking membrane was stored in a desiccator until further processed.

Strip Construction

Dye pad was attached to plastic base right below the bottom of nitrocellulose membrane and the filter pad is attached adjacent to the dye pad. The plastic plate then was cut into a plurality of strips 60 mm in length and 4 mm in width so that each contains a linear array of nitrocellulose membrane, dye pad and filter pad.

Assay Method and Result:

When 70 micro liter sample was added into filter pad, a detectable signal began to appear in the assay indicia zone after incubation when the strip was exposed to UV light.

Example 5

Preparation of hCG Test Strip Using Colloidal Gold

Preparation of Gold Sol 1400 ml of deionized water was brought to a boil. Hydroauric acid (299 to 305 mg) was added, and boiling continued for 5 minutes. Sodium citrate (440 mg) dissolved in 10 ml of distilled water was poured into the gold solution and the solution boiled for another 10 minutes. The solution was allowed to cool to ambient room temperature.

Preparation of Label pH of gold sol was adjusted to 6.8 with 40 mM potassium carbonate. Same monoclonal antibody used in Example 4 was added to 50 ml of gold solution which was stirred vigorously for 30 min at ambient temperature. 1 ml of 15% bovine serum albumin was added, and the solution was continuously stirred for approximately 15 min at ambient temperature. Colloidal gold-monoclonal antibody conjugate was recovered by centrifugation at 10,000 rpm in GSA rotor for 1 hr, discarding the supernatant and suspending the resultant pellet in 25 ml of 2% bovine serum albumin in 10 mM sodium phosphate, pH 7.5. The suspension was then spun down at 10,000 rpm for 1 hr in GSA rotor. The supernatant once again was discarded and the pellet suspended in 6 ml of 2% bovine serum albumin in 10 mM sodium phosphate, pH 7.5.

Preparation of Dye Pad

The glass fiber filter was prepared by impregnating with a solution containing anti-hCG antibody coated colloidal gold, 0.2% tween-20, 0.25% bovine serum albumin, 0.5% sucrose, 10 mM sodium phosphate, pH 7.5 to rectangular piece of glass fiber filter measuring 8 mm×305 mm and dried under constant vacuum in a lyophilizer. The pad was stored dry in a desiccator until use.

Preparation of Filter Pad

The glass fiber filter was treated with a solution of 0.05% Tween-20, 2% of sucrose, 1% of BSA and 100 mM sodium phosphate, pH 7.4, and then air dried at room temperature.

Immobilization of Antibody on Membrane

A double sided transparent tape (305 mm×25 mm size) was attached to 20 mm from the bottom of the thin plastic plate (305×60 mm). A nitrocellulose membrane was cut to 305 mm×25 mm size and attached directly on the top of the double sided tape. An assay indicia zone of immobilized test line for hCG was defined on the 9 mm from the bottom of the membrane by spraying 30 micro liter of solution of 1 mg/ml goat anti-troponin I antibody in 10 mM PBS, pH 7.5. For control band, 1 mg/ml of polyclonal anti-mouse IgG antibody was defined on the 13 mm from the bottom of the membrane by spraying. After spraying, the membrane was dried at ambient temperature for approximately 12 hours. The base and wicking membrane were stored in a desiccator until further processed.

Strip Construction

Dye pad was attached to plastic base right below the bottom of nitrocellulose membrane and the filter pad was attached adjacent to the dye pad. The plastic plate then was cut into a plurality of strips 60 mm in length and 4 mm in width so that each contains a linear array of nitrocellulose membrane, dye pad and filter pad.

Assay Method and Result:

When 70 micro liter sample was added into filter pad, a detectable signal began to appear in the assay indicia zone after incubation.

Example 6

Comparison of the Sensitivity of the Strips Prepared Using Each Method

The strip prepared in Example 4 and the strip prepared in Example 5 were tested to compare the sensitivity. The strip prepared in Example 4 showed 1.5 mIU/ml of sensitivity while the strip prepared in Example 5 showed 15 mIU/ml of sensitivity. The strip prepared using europium nanoparticle showed about 10 times more sensitive result than the strip prepared using colloidal gold.

Example 7

Preparation of Dengue Virus Test Strip Using Europium Chelate Nanoparticle

Preparation of Oligonucleotides Coated Nanoparticle

The carboxyl group of europium chelate nanoparticles were activated with 10 mmol/L N-(3-dimethylaminopropyl)-N'-ethylcarbodiimide and 100 mmol/L N-hydroxysulfosuccinimide for 30 min. The activated particle washed once with 50 mM MES buffer, pH 6.1. 20 mM/L oligonucleotide with carriers such as bovine serum album was added. After 2 hour incubation, the oligonucleotide coated particles were washed three times with 50 mM MES buffer, pH 6.1.

Preparation of Dye Pad

The glass fiber filter was prepared by impregnating with a solution containing oligonucleotides coated nanoparticle, 0.2% tween-20, 0.25% bovine serum albumin, 0.5% sucrose, 10 mM sodium phosphate, pH 7.5 to rectangular piece of glass fiber filter measuring 8 mm×305 mm and dried under constant vacuum in a lyophilizer. The pad was stored dry in a desiccator until use.

Preparation of Filter Pad

The glass fiber filter was treated with a solution of 0.05% Tween-20, 2% of sucrose, 1% of BSA and 100 mM sodium phosphate, pH 7.4, and then air dried at room temperature.

Immobilization of Oligonucleotide on Membrane

A double sided transparent tape (305 mm×25 mm size) was attached to 20 mm from the bottom of the thin plastic plate (305×60 mm). A nitrocellulose membrane was cut to 305 mm×25 mm size and attached directly on the top of the double sided tape. An assay indicia zone of immobilized test line for dengue virus specific oligonucleotide was defined on the 9 mm from the bottom of the membrane by spraying 30 micro liter of solution of 1 mg/ml oligonucleotide-BSA conjugate in 10 mM PBS, pH 7.5. After spraying, the membrane was dried at ambient temperature for approximately 12 hours. The base and wicking membrane was stored in a desiccator until further processed.

Strip Construction

Dye pad was attached to plastic base right below the bottom of nitrocelluolse membrane and the filter pad is attached adjacent to the dye pad. The plastic plate then was cut into a plurality of strips 60 mm in length and 4 mm in width so that each contains a linear array of nitrocellulose membrane, dye pad and filter pad.

Assay Method and Result:

When 70 micro liter sample was added into filter pad, a detectable signal began to appear in the assay indicia zone after incubation when the strip was exposed to UV light.

Example 8

Preparation of Dengue Virus Test Strip Using Europium Chelate Nanoparticle with Polymerase Chain Reaction Preparation of Streptavidin Coated Nanoparticle The carboxyl group of europium chelate nanoparticles were activated with 10 mmol/L N-(3-dimethylaminopropyl)-N'-ethylcarbodiimide and 100 mmol/L N-hydroxysulfosuccinimide for 30 min. The activated particle washed once with 50 mM MES buffer, pH 6.1. 20 mM/L strepatavidine was added. After 2 hour incubation, the streptavidin coated particles were washed three times with 50 mM MES buffer, pH 6.1.

Preparation of Dye Pad

The glass fiber filter was prepared by impregnating with a solution containing streptavidin coated nanoparticle, 0.2% tween-20, 0.25% bovine serum albumin, 0.5% sucrose, 10 mM sodium phosphate, pH 7.5 to rectangular piece of glass fiber filter measuring 8 mm×305 mm and dried under constant vacuum in a lyophilizer. The pad was stored dry in a desiccator until use.

Preparation of Filter Pad

The glass fiber filter was treated with a solution of 0.05% Tween-20, 2% of sucrose, 1% of BSA and 100 mM sodium phosphate, pH 7.4, and then air dried at room temperature.

Immobilization of Anti-Hapten Antibodies on Membrane

A double sided transparent tape (305 mm×25 mm size) was attached to 20 mm from the bottom of the thin plastic plate (305×60 mm). A nitrocellulose membrane was cut to 305 mm×25 mm size and attached directly on the top of the double sided tape. An assay indicia zone of immobilized test line for anti-hapten antibody was defined on the 9 mm from the bottom of the membrane by spraying 30 micro liter of solution of 1 mg/ml streptavidin oligonucleotide-BSA conjugate in 10 mM PBS, pH 7.5. After spraying, the membrane was dried at ambient temperature for approximately 12 hours. The base and wicking membrane was stored in a desiccator until further processed.

Strip Construction

Dye pad was attached to plastic base right below the bottom of nitrocelluolse membrane and the filter pad is attached adjacent to the dye pad. The plastic plate then was cut into a plurality of strips 60 mm in length and 4 mm in width so that each contains a linear array of nitrocellulose membrane, dye pad and filter pad.

Assay Method and Result:

When 2 micro liter sample and 70 micro liter of develop solution were added into the filter pad, a detectable signal began to appear in the assay indicia zone after incubation when the strip was exposed to UV light.

All of the references cited herein are incorporated by reference in their entirety.

Those skilled in the art will recognize, or be able to ascertain using no more than routine experimentation, many equivalents to the specific embodiments of the invention specifically described herein.

We claim:

1. An analyte detection lateral assay format apparatus having at least one reservoir area, and a wicking membrane, wherein a specific binding partner to the analyte, which is covalently labeled with a particle comprising a europium (III) chelate having about 30,000 to 1,000,000 europium(III) atoms per particle, is impregnated on the reservoir area; and at least one chemical or biological component selected from the group consisting of an antigen, an antibody, a nucleic acid, biotin or biotin analogue, streptavidin, avidin and a hapten is immobilized on the wicking membrane, wherein said analyte, if present, is bound by said specific binding partner.

2. The apparatus according to claim 1, wherein the specific binding partner binds an antigen, an antibody, a nucleic acid or a hapten as said analyte if present.

3. The apparatus according to claim 1, wherein the specific binding partner is selected from the group consisting of an antigen, an antibody, a nucleic acid, biotin or biotin analogue, streptavidin, avidin and a hapten.

4. A method of determining or detecting the presence of an analyte in a sample comprising applying an amount of the sample to the apparatus according to claim 1, wherein the sample migrates to the wicking membrane where a specific reaction occurs, wherein presence of a signal indicates that the analyte is present in the sample, wherein the signal is generated by a europium(III) chelate in a particle in complex with said analyte, and detecting presence of the analyte.

5. The method according to claim 4, wherein the sample is a biological sample.

6. The method according to claim 5, wherein the sample is selected from the group consisting of blood, serum, plasma, urine, saliva, sweat and liquid media processed from a biological or environmental sample.

7. The method according to claim 4, wherein the analyte is selected from the group consisting of an antigen, an antibody, a nucleic acid and a hapten.

8. The method according to claim 4, wherein the specific reaction is with a chemical or biological component selected from the group consisting of an antigen, an antibody, a nucleic acid, biotin or biotin analogue, streptavidin, avidin and a hapten.

9. The method according to claim 4, wherein the analyte is specific to a pathogen.

10. A kit comprising a container which comprises the apparatus according to claim 1 and instructions on using the kit.

* * * * *